United States Patent [19]

Tomoff

[11] 4,204,770
[45] May 27, 1980

[54] GRAPHITE FURNACE BORE TEMPERATURE MEASUREMENTS IN FLAMELESS ATOMIC ABSORPTION SPECTROSCOPY

[75] Inventor: Toma Tomoff, Überlingen, Fed. Rep. of Germany

[73] Assignee: Bodenseewerk Perkin-Elmer & Co., GmbH, Uberlingen, Fed. Rep. of Germany

[21] Appl. No.: 891,796

[22] Filed: Mar. 29, 1978

[30] Foreign Application Priority Data

Apr. 26, 1977 [DE] Fed. Rep. of Germany ....... 2718416

[51] Int. Cl.² .................................................. G01J 3/00
[52] U.S. Cl. ..................................... 356/312; 356/244
[58] Field of Search .......................... 356/85, 244, 312

[56] References Cited

U.S. PATENT DOCUMENTS 3,941,487  3/1976  Ehret et al. ........................... 356/244
3,982,834  9/1976  Tamm ................................... 356/244

OTHER PUBLICATIONS

"A Very Inexpensive Temperature Monitor for Flameless Atomic Absorption Apparatus"; Watne et al.; Applied Spectroscopy; pp. 71 & 72; vol. 30 #1; Jan.-Feb. 1976.

Primary Examiner—Vincent P. McGraw
Attorney, Agent, or Firm—S. A. Giarratana; F. L. Masselle; E. T. Grimes

[57] ABSTRACT

Inaccuracies resulting from measuring the internal temperature of absorption spectrophotometer graphite tube furnaces by pyrometric measurements of a spot on the external surface of the graphite tube are overcome by a novel arrangement in which the pyrometer detector measures the interior through the tube end and at an angle that permits a view of the entire interior length without interfering with the spectrophotometer sample beam.

5 Claims, 2 Drawing Figures

GRAPHITE FURNACE BORE TEMPERATURE MEASUREMENTS IN FLAMELESS ATOMIC ABSORPTION SPECTROSCOPY

BACKGROUND OF THE INVENTION

In flameless absorption spectrophotometer measurements, a sample of material to be analyzed is placed in a tubular graphite furnace which is electrically heated so that the sample first dries, then ashes, and is eventually heated to the point at which the various elements in the sample become atomized. When the particular element or elements to be measured have been released into their atomic state, a light beam originating from a resonant line-emitting source is passed through the heated furnace tube and into a monochromator and detector, the circuitry of which determines the concentration of the desired element in the sample by measuring the intensities of appropriate portions of the resulting beam after the desired atomic element has absorbed its characteristic resonant lines.

The temperature to which the graphite tube is to be heated is important since insufficient heating may atomize portions of the sample but not the desired element to be measured, and excessive heat may atomize such more than is necessary and release undesired atoms that may interfere with the desired measurements. Generally, such graphite tube measurements are made by an optical pyrometric detector that is positioned to observe a spot on the exterior surface of the heated graphite tube and near its center where the sample is injected and at the location of the highest heat of the tube. The pyrometer output is then scaled to a particular factor to approximate the interior heat of the tube, and this scaled signal is then applied to a heat controller which controls the electrical current through the graphite tube to reach and maintain the desired atomizing temperature of the element to be measured.

While pyrometric measurements have generally proved to be quite satisfactory, there are difficulties that result in erroneous temperature measurements when a spot on the tube exterior is measured. For example, the graphite tube is normally supported between electrodes which, in turn, are held between large cooling jackets provided to prevent heat damage to associated hardware. The spacing between the surrounding electrodes must be sufficiently large to prevent electrical short-circuiting between the electrodes but must be maintained small to prevent heat escape from the graphite tube. It is, therefore, extremely difficult to provide sufficient space to image a pyrometer against the graphite tube surface. Furthermore, to eliminate oxygen from the area of the heated tube and thereby prevent burning of the tube, it is necessary to circulate an inert gas around the outer surface of the tube. Because of the necessary electrical insulating spacing between the electrodes and because there is an additional opening in the tube and one electrode to permit insertion of a sample into the graphite tube, a considerable amount of this inert gas will normally escape into the atmosphere and it is therefore necesssary that large quantities of this inert gas be admitted into the area between the exterior of the graphite tube and the interior of the electrodes. This flow of inert gas causes variations in temperature of the external surface of the graphite tube and consequently an inaccurate temperature measurement by a pyrometer detector viewing that external tube surface.

BRIEF DESCRIPTION OF THE INVENTION

The object of this invention is to provide a means for accurately and conveniently measuring the temperature within the bore of a spectrophotometer by pyrometric measuring means that overcome the disadvantages described above.

Briefly described, the invention is for a graphite tube mounting structure which permits an externally positioned pyrometer detector to observe the entire internal longitudinal length of the tube through the bore provided for passage of the sample light beam. This eliminates the need for additional radial holes through the electrodes that support the graphite tube and therefore help maintain a constant temperature of the tube. It has been found that the accuracy of this type of measurement is not affected by internal smoke which is generated particularly during the ashing process, since the smoke is at the same internal temperature. The pyrometric measurement through the bore is made by locating the pyrometer so that its viewing path is inclined with respect to the longitudinal axis of the tube and so that the viewing axis passes through the bore of the cooling jacket and electrodes and into the end of the graphite tube to the central portion or section of the tube normally at the highest temperature. Such an arrangement does not require an optical system for imaging an area and therefore does not present the problems of spectral transparency of the optical elements heretofore encountered.

The pyrometer is directed toward a spot in the center of the internal surface of the graphite tube but its observation angle observes the entire internal length of the tube. Therefore, an average temperature will be made, since the detector will receive not only radiation from the high-temperature central zone of the tube, but also radiation from the cooler edge zones. This average reading can be accurately and easily scaled to correct to the temperature at the central atomizing section of the tube. However, without such scaling, accuracy is not materially affected since, as is well-known, radiation increases with the fourth power of temperature so that the zone having the highest temperature will dominate the measurement.

BRIEF DESCRIPTION OF THE DRAWINGS

In the drawings which illustrate a preferred embodiment of the invention.

DESCRIPTION OF THE PREFERRED EMBODIMENT

Figure 1:
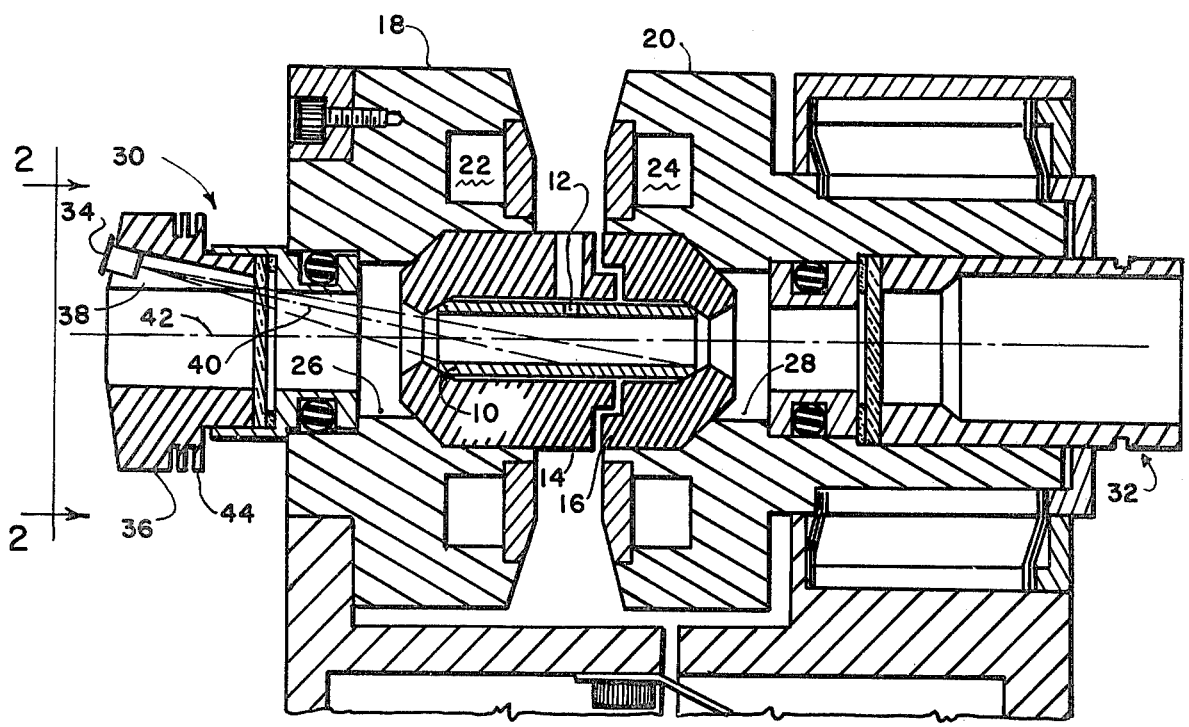
FIG. 1 is a sectional elevation view illustrating the graphite tube furnace in its associated structure that incorporates the bore-sighting pyrometer detector of the invention.

Referring to FIG. 1, numeral 10 designates the graphite sample tube of an absorption spectrophotometer. At substantially the mid-point in the length of the tube 10 is a radial bore 12 which provides a port for introducing a sample into the tube. The ends of tube 10 are tapered to mate with the conical end sections of electrodes 14 and 16. Electrodes 14 and 16 have coaxial tubular bores sufficiently larger than the external diameter of the tube 10 to provide a space between tube and electrodes which, during operation, permits a flow of inert gas around the external surface of the tube 10.

The external surfaces of electrodes 14 and 16 are cylindrical and are fitted into cooling jackets 18 and 20, respectively, each of which are provided with an annular chamber 22 and 24, respectively, for the circulation of a liquid coolant. As illustrated in FIG. 1, cooling jackets 18 and 20 are provided with coaxial tubular bores 26 and 28, respectively, the adjacent faces of which are counterbored with enlarged sections to accommodate the electrodes 14 and 16. The smaller diameter outer section of the bores 26 and 28 are also enlarged to accommodate window holders 30 and 32, respectively, each of which contains an optical window seal for preventing escape of gases through the bore and yet permitting transmission of the sample measuring beam of the absorption spectrophotometer to pass through the hollow bore of the window holder 30, the bore 26 of the cooling jacket 18, the open bore of the electrode 14, tube 10, and on through the corresponding apertures in the opposite end of the structure.

Figure 2:
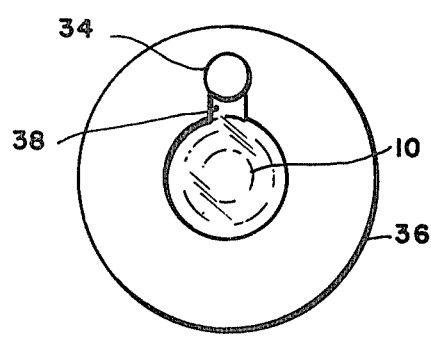
FIG. 2 is a view taken along the lines 2—2 of FIG. 1.

As illustrated in FIG. 2, a pyrometer detector 34 is positioned in the end surface of the enlarged end 36 of the window holder 30. The detector 34 is positioned above and outside of the hollow bore of the holder 30 and, as best shown in FIG. 1, is positioned to observe the inner bore of the graphite tube 10 through a channel 38 that is cut in the holder 30 between pyrometer 34 and the hollow bore of the holder 30. Therefore, as shown in FIG. 1, the pyrometer detector 34 is located in this inclined channel so that the detector center line 40 extends at an inclined angle with respect to the center line 42 of the graphite tube 10 and its associated structures. The detector center line 40 is directed through the bore 26 of the cooling jacket 18 into the graphite tube 10 in the direction such that it intersects the inner surface of the graphite tube 10 at approximately the center of the tube. The detecting angle will therefore extend substantially along the entire internal length of the graphite tube 10 so that the pyrometric detector 34 will generate a corresponding electrical signal without the necessity of auxiliary imaging optics.

To prevent heat damage to the pyrometric detector 34 from the high temperatures radiating from the interior of the structure, it is desirable to provide the enlarged end 36 of the holder 30 with suitable heat-dissipating fins 44.

What is claimed is:

1. In an absorption spectrophotometer sample furnace having a graphite sample atomizing tube mounted between electrodes supported by cooling structures, said graphite tube, said electrodes and said cooling structures having coaxial longitudinal bores to permit passage of a spectrophotometer measuring beam, a temperature sensing means for measuring the temperature of said graphite tube, said temperature sensing means comprising a pyrometric detector positioned with respect to the logitudinal center line of said coaxial longitudinal bores to sense the internal temperature of the graphite tube through the end of said tube and so that the entire length of the surface of said graphite tube is within the field of view of said detector, said detector being mounted to the exterior end surface of a window holder coaxial with center line of said longitudinal bores, said detector being positioned so that the center line of its field of view is non-symmetrical to and inclined at an angle from the center line of said bores and is directed toward the central portion of the interior surface of said graphite tube.

2. The temperature-sensing means claimed in claim 1 wherein said window holder has an enlarged cylindrical end section provided with annular external cooling flanges.

3. An absorption spectrophotometer comprising a pair of axially spaced electrodes having tubular bores on a common axis for coaxially receiving a graphite sample atomizing tube, a pair of jackets having tubular bores coaxial with one another and said common axis for coaxially receiving respective electrodes and enabling passage of a spectrophotometer measuring beam through said jackets, said electrodes, and the atomizing tube carried by said electrodes, a temperature sensing means for measuring the temperature of the atomizing tube, said temperature sensing means including a pyrometric detector carried by said spectrophotometer at a location offset from said axis and disposed non-symmetrically with respect to said axis to sense the internal temperature of the graphite tube through an end of the tube and an end of one of the electrodes.

4. The spectrophotometer according to claim 3 including a window holder carried by one of said jackets coaxial with said bores and axially spaced from said one electrode end on the side thereof remote from the other electrode, said detector being carried by said window holder with the center line of its field of view non-symmetrical and inclined at an angle to said axis and directed toward the central portion of the interior surface of the graphite tube.

5. The spectrophotometer according to claim 4 in combination with said graphite sample atomizing tube.

* * * * *